(12) United States Patent
Parks

(10) Patent No.: US 11,376,301 B2
(45) Date of Patent: *Jul. 5, 2022

(54) COMPOSITIONS AND METHODS FOR IMPROVING VISIBILITY OF THE GASTROINTESTINAL TRACT FOR ENDOSCOPY PROCEDURES

(71) Applicant: Advanced Health Solutions LLC, Gig Harbor, WA (US)

(72) Inventor: Jill Parks, Gig Harbor, WA (US)

(73) Assignee: Advanced Health Solutions LLC, Gig Harbor, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/747,111

(22) Filed: Jan. 20, 2020

(65) Prior Publication Data

US 2021/0220425 A1 Jul. 22, 2021

(51) Int. Cl.

| *A61K 36/906* | (2006.01) |
| *A61K 31/12* | (2006.01) |
| *A61K 47/12* | (2006.01) |
| *A61K 47/10* | (2017.01) |
| *A61K 47/22* | (2006.01) |
| *A61K 47/02* | (2006.01) |

(52) U.S. Cl.
CPC ............ *A61K 36/906* (2013.01); *A61K 31/12* (2013.01); *A61K 47/02* (2013.01); *A61K 47/10* (2013.01); *A61K 47/12* (2013.01); *A61K 47/22* (2013.01)

(58) Field of Classification Search
None
See application file for complete search history.

(56) References Cited

U.S. PATENT DOCUMENTS

| 2009/0220625 A1* | 9/2009 | Herrmann | A61K 31/045 424/756 |
| 2012/0219642 A1* | 8/2012 | Nizam | A61K 9/0053 424/724 |
| 2016/0235284 A1* | 8/2016 | Yoshida | C11D 7/265 |
| 2018/0104225 A1* | 4/2018 | Kang | A23L 2/52 |

OTHER PUBLICATIONS

Zadeh et al., "Physiological and pharmaceutical effects of Ginger (*Zingiber officinale* Roscoe) as a valuable medicinal plant", European Journal of Experimental Biology, 4(1), 2014, pp. 87-90. (Year: 2014).*

Petersen et al., "Multisociety guideline on reprocessing flexible GI endoscopes: 2016 update", Gastrointestinal Endoscopy, 85(2), 2017, pp. 282-294. (Year: 2017).*

Benmassaoud et al., "CAG Position Statement: The Impact of Simethicone on Endoscope Reprocessing," Canadian Association of Gastoenterology (Jul. 10, 2017).

"2020 Guidance on Decontamination of Equipment for Gastrointestinal Endoscopy," The Report of a Working Party of the British Society of Gastoenterology Endoscopy Committee, British Society of Gastroenterology (2022).

Loyola, et al., "Guideline for Use of High-Level Disinfectants & Sterilants in the Gastroenterology Setting," Society of Gastroenterology Nurses and Associates, Inc. (2017).

Barakat, et al., "Simethicon is retained in endoscopes despite reprocessing: impact of its use on working channel fluid retention and adenosine triphosphate bioluminescence values (with video)," HHS Public Access Author manuscript (PMC Jan. 1, 2020).

Devereaux, et al., "Simethicon use during gastrointestinal endoscopy: Position statement of the Gastroenterological Society of Australia," Journal of Gastroenterology and Hepatology 34 (2019) 2086-2089.

Olympus, "RE: Use of simethicone and other non-water soluble additives with Olympus flexible endoscopes," (Jun. 29, 2018).

"Infections Associated with Reprocessed Duodenoscopes," FDA U.S. Food & Drug Administration website (https://www.fda.gov/medical-devices/reprocessing-reusable-medical-devices/infections-associated-reprocessed-duodenoscopes) (Aug. 29, 2019).

* cited by examiner

*Primary Examiner* — Melissa L Fisher
(74) *Attorney, Agent, or Firm* — Terrence J. Edwards; TechLaw Ventures, PLLC

(57) ABSTRACT

Compositions and methods for improving gastrointestinal function and reducing the presence of gas bubbles in a gastrointestinal tract. A method includes administering a composition to a user during an endoscopy procedure for reducing a presence of gas bubbles in a gastrointestinal tract of a user. The composition includes an effective amount of ginger root extract for reducing the presence of the gas bubbles in the gastrointestinal tract of the user, and further includes propylene glycol and sodium chloride.

15 Claims, 5 Drawing Sheets

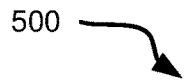

Administering A Composition To A User During An Endoscopy Procedure, Wherein The Composition Is Effective For Reducing The Presence Of Gas Bubbles In A Gastrointestinal Tract Of The User.
502

Wherein The Composition Comprises An Effective Amount Of Ginger Root Extract For Reducing The Presence Of The Gas Bubbles In The Gastrointestinal Tract Of The User.
504

Wherein The Composition Comprises Propylene Glycol.
506

FIG. 5

600 

```
┌─────────────────────────────────────────────────────────────────────────┐
│ Administering A Composition To A User During A Colonoscopy Procedure,   │
│ Wherein The Composition Is Effective For Reducing The Presence Of Gas   │
│ Bubbles In A Gastrointestinal Tract Of The User.                        │
│                                  602                                    │
└─────────────────────────────────────────────────────────────────────────┘
                                     │
                                     ▼
┌─────────────────────────────────────────────────────────────────────────┐
│ Wherein The Composition Comprises An Effective Amount Of Ginger Root    │
│ Extract For Reducing The Presence Of The Gas Bubbles In The             │
│ Gastrointestinal Tract Of The User.                                     │
│                                  604                                    │
└─────────────────────────────────────────────────────────────────────────┘
                                     │
                                     ▼
┌─────────────────────────────────────────────────────────────────────────┐
│            Wherein The Composition Comprises Propylene Glycol.          │
│                                  606                                    │
└─────────────────────────────────────────────────────────────────────────┘
                                     │
                                     ▼
┌─────────────────────────────────────────────────────────────────────────┐
│     Visualizing An Interior Of The Gastrointestinal Tract Of The User   │
│                            With A Colonoscope.                          │
│                                  608                                    │
└─────────────────────────────────────────────────────────────────────────┘
                                     │
                                     ▼
┌─────────────────────────────────────────────────────────────────────────┐
│         Processing The Colonoscope To Remove Traces Of The Composition. │
│                                  610                                    │
└─────────────────────────────────────────────────────────────────────────┘
```

Administering A Composition To A User During A Colonoscopy Procedure, Wherein The Composition Is Effective For Reducing The Presence Of Gas Bubbles In A Gastrointestinal Tract Of The User.
702

Wherein The Composition Comprises An Effective Amount Of Ginger Root Extract For Reducing The Presence Of The Gas Bubbles In The Gastrointestinal Tract Of The User.
704

Wherein The Composition Comprises Propylene Glycol And Sodium Chloride.
706

Visualizing An Interior Of The Gastrointestinal Tract Of The User With A Colonoscope.
708

Processing The Colonoscope To Remove Traces Of The Composition.
710

FIG. 7

COMPOSITIONS AND METHODS FOR IMPROVING VISIBILITY OF THE GASTROINTESTINAL TRACT FOR ENDOSCOPY PROCEDURES

TECHNICAL FIELD

The disclosure relates generally to compositions and methods for reducing the presence of gas bubbles in the digestive system and particularly relates to compositions and methods for reducing the presence of gas bubbles in the gastrointestinal tract during an endoscopy procedure.

BACKGROUND

The digestive system includes the gastrointestinal tract and other accessory organs of digestion. Digestion involves the breakdown of food into smaller components until nutrients can be absorbed and assimilated into the body. The gastrointestinal tract is an organ system within many animals that takes in food, digests the food to extract and absorb energy and nutrients, and expels the remaining waste. The mouth, esophagus, stomach, and intestines are part of the gastrointestinal tract.

The digestive system includes complicated organs performing complex chemical and biological processes. Because the digestive system is very complex, many individuals suffer ailments of the digestive system that may be chronic or transitory. Common ailments of the digestive system include, for example, gastroesophageal reflux disease, irritable bowel syndrome, gallstones, constipation, stomach pains, excessive gas, cancer, tissue abnormalities such as polyps, and others. In some instances, the most effective means for examining the gastrointestinal tract includes viewing the interior of the large intestine by way of a colonoscopy. A colonoscopy is an imaging procedure that involves inserting a specialized endoscope (referred to as a colonoscope) into a patient to view the interior space of the large intestine.

However, the effectiveness of a colonoscopy is highly dependent on the patient's preparation for the colonoscopy and further on the presence of gas bubbles in the large intestine. The digestive system naturally produces gas, and therefore it is highly likely that a patient will have gas bubbles present in the large intestine during a colonoscopy procedure. The presence of gas bubbles in the large intestine obstructs the view of the walls of the large intestine and thereby negatively impacts visibility during the procedure. In some instances, a medical practitioner will flush the patient's large intestine with simethicone during the colonoscopy. Simethicone is known to reduce the surface tension of bubbles to reduce and even eliminate the presence of gas bubbles. However, simethicone is not water soluble and is therefore very difficult to clean off the colonoscope. Simethicone can harbor bacteria and biofilm. The use of simethicone during colonoscopy procedures can lead to the transmission of disease from patient-to-patient and is therefore not recommended. Therefore, there is a need for improved means for reducing the presence of gas bubbles during colonoscopy procedures without negatively impacting the ability to clean and repurpose the colonoscope after the procedure.

In light of the foregoing, disclosed herein are compositions and methods for reducing the presence of gas bubbles in the gastrointestinal tract during an endoscopy procedure without negatively impact the ability to clean and repurpose the endoscopic equipment.

BRIEF DESCRIPTION OF THE DRAWINGS

Non-limiting and non-exhaustive implementations of the present disclosure are described with reference to the following figures, wherein like reference numerals refer to like parts throughout the various views unless otherwise specified. Advantages of the present disclosure will become better understood with regard to the following description and accompanying drawings where:

FIG. 5 is a schematic flow chart diagram of a method for reducing or eliminating gas bubbles in a gastrointestinal tract during an endoscopy procedure;

FIG. 6 is a schematic flow chart diagram of a method for reducing or eliminating gas bubbles in a gastrointestinal tract and for processing a colonoscope following a colonoscopy procedure; and FIG. 7 is a schematic flow chart diagram of a method for reducing or eliminating gas bubbles in a gastrointestinal tract and for processing a colonoscope following a colonoscopy procedure.

DETAILED DESCRIPTION

Figure 1:
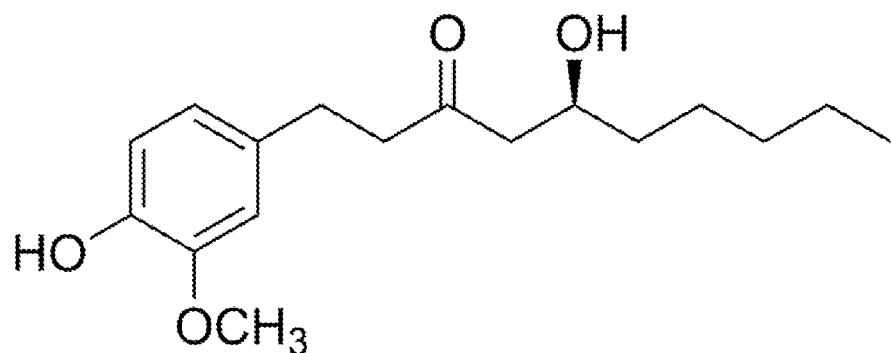
FIG. 1 illustrates the chemical formula of 6-gingerol.

The digestive system is an important component of the body. The digestive system includes the gastrointestinal (GI) tract whereby food is digested by the body. The gastrointestinal tract begins with the mouth and includes the esophagus, stomach, small intestine, large intestine, rectum, and anus. The human gastrointestinal tract is a single tube which is approximately nine meters long in relaxed condition. A disorder in any portion of the gastrointestinal tract can result in various malfunctions such as diseases of the digestive system and cancer.

Some issues associated with the gastrointestinal tract are best examined by way of an endoscopic imaging procedure referred to as a colonoscopy. A colonoscopy is an exam for detecting changes or abnormalities in the gastrointestinal tract. During a colonoscopy, a specialized endoscope referred to as a colonoscope is inserted into the large intestine of the patient. The colonoscope includes a long, flexible tube that may be inserted into the patient by way of the rectum. The colonoscope includes a small video camera at the distal end of the device that allows a practitioner or computer program to view the interior of the colon. Tissue samples for biopsies may also be taken during the colonoscopy. If necessary, polyps or other types of abnormal tissue can be removed with the colonoscope during the colonoscopy.

The efficacy of a colonoscopy is highly dependent on preparation of the large intestine. Preparation for a colonoscopy may include the administration of substances for reducing the presence of gas bubbles within the large intestine. However, despite such preparation, it is common for gas bubbles to still be present in the large intestine during the colonoscopy procedure. In such instances, it is beneficial to flush the large intestine with compositions capable of reducing or eliminating the presence of gas bubbles.

There are some substances known in the art that are effective for reducing the presence of gas bubbles during a colonoscopy procedure. One substance that is commonly used for flushing the large intestine during a colonoscopy is simethicone. However, simethicone is not water soluble and can harbor harmful bacteria and viruses. Simethicone can form a film on the colonoscope that is very challenging to remove prior to the colonoscope being cleaned and disinfected for reuse. Because the simethicone is difficult to remove, the simethicone can cause harmful bacteria and viruses to remain on the colonoscope and then be transmitted to a subsequent patient even after the colonoscope has been disinfected for reuse. If the colonoscope is not fully disinfected, a disease present in the colon of a first patient can be transmitted to one or more subsequent patients because the disease will adhere to the colonoscope during the colonoscopy for the first patient.

Simethicone is an anti-foaming agent that is used to reduce bloating, discomfort, or pain caused by gas. The colon can be flushed with simethicone and sodium phosphate during a colonoscopy to improve visibility of the colon by diminishing air bubbles. Chemically, simethicone is a mixture of polydimethylsiloxanes that work by reducing the surface tension of air bubbles and causing the coalescence of small bubbles into larger ones that can pass more easily. While simethicone is shown to be effective for improving visibility during a colonoscopy, the use of simethicone during a colonoscopy is undesirable and potentially unsafe. Simethicone is not water soluble and therefore adheres to the colonoscope and can trap diseases that are present in a patient's colon. When simethicone is used during a colonoscopy, the colonoscope is then difficult to clean and can harbor dangerous bacteria and viruses that can be transmitted to subsequent patients despite the performance of standard cleaning and disinfection procedures. Therefore, there is a desire to improve colonoscopy visibility by reducing gas bubbles without negatively impacting the ability to clean and disinfect the colonoscope after use.

In light of the foregoing, disclosed herein are compositions and methods for reducing gas bubbles during a colonoscopy without negatively impacting the ability to disinfect the colonoscope after use. In an embodiment, a composition includes ginger root extract and propylene glycol. The composition is effective for reducing gas bubbles present in the gastrointestinal tract. The composition may be ingested by a patient prior to a colonoscopy to reduce the presence of gas bubbles in the patient's large intestine and therefore prepare the patient for a colonoscopy. Additionally, the composition may flow through the colonoscope to flush the patient's colon during the colonoscopy.

Further, embodiments of the disclosure include compositions and methods for improving gastrointestinal function and reducing symptoms of gas in the gastrointestinal tract. The compositions and methods disclosed herein are water soluble to increase absorption of the active ingredients and improve the efficacy of the active ingredients. In an embodiment, a composition includes ginger root extract and specifically includes 6-gingerol and 6-shogaol. The composition includes an effective amount of ginger root extract for reducing gas in the gastrointestinal tract and improving gastrointestinal function.

Issues associated with the digestive system and the gastrointestinal (GI) tract are commonly treated with synthetic drugs. Synthetic drugs are expensive and cause genetic and metabolic alterations that can be unsafe for some individuals. Therefore, there is a desire to treat gastrointestinal issues with compositions including natural ingredients and medicinal plants.

Ginger (*Zingiber officinale*) is a member of the Zingiberaceae family. Chemical analysis of ginger shows that it includes over 400 different compounds. The major components in ginger rhizomes are carbohydrates (50-70%), lipids (3-8%), terpenes, and phenolic compounds. Terpene components of ginger include zingiberene, β-bisabolene, α-farnesene, β-sesquiphellandrene, and α-curcumene. Phenolic compounds include gingerol, paradols, and shogaol. Gingerol and shogaol are found in higher quantities than other components of ginger. Ginger further includes amino acids, raw fiber, ash, protein, phytosterols, vitamins, and minerals.

The aromatic constituents of ginger include zingiberene and bisabolene. The pungent constituents include the gingerol-related compounds and the shogaol-related compounds. The gingerol- and shogaol-related compounds within ginger rhizome include 6-paradol, 1-dehydrogingerdione, and 6-diarylhgeptanoids.

Ginger and its components have been shown to modulate a wide range of signaling molecules. Ginger may upregulate or downregulate the gene expression of multiple different genes depending on the target and cellular context. Ginger extract increases production of antioxidant enzymes including reduced glutathione (GSH), superoxide dismutase (SOD), and glutathione peroxidase. Ginger additionally targets phase II detoxification enzymes as well as nuclear localization of the Nrf2 pathway.

Additionally, a number of targets of ginger and its components have been documented in different cancer prevention models, including transcription factors, enzymes, inflammatory mediators, protein kinases, drug resistance proteins, adhesion molecules, growth factor receptors, cell-cycle regulatory proteins, cell-survival proteins, chemokines, and chemokine receptors. In different gastrointestinal cancers, ginger extract inhibits transcription factor NF-kB, inflammatory cytokine, TNF-α, and other enzymes and proteins, which include xanthine oxidase and myeloperoxidase.

The active ingredients of ginger, including 6-gingerol and 6-shogaol, target several cellular molecules that contribute to cell survival, cell proliferation, and angiogenesis. 6-gingerol modulates NF-κB, STAT3, Rb, MAPK, PI3K, Akt, ERK, cIAP1, cyclin A, Cdk, cathepsin D, and caspase-3/7. Similarly, 6-shogaol targets NF-κB, STAT3, MAPK, PI3k/Akt $Ca^{2+}$ signals, COX-2, cyclin D1, survivin, cIAP-1, XIAP, Bcl-2, MMP-9, caspase activation, ER stress, and eIF2α. Besides these, ginger component zerumbone modulates NF-κB, p53 VEGF, p21, and CXCR4 expression.

In the following description of the disclosure, reference is made to the accompanying drawings, which form a part hereof, and in which is shown by way of illustration specific implementations in which the disclosure may be practiced. It is understood that other implementations may be utilized, and structural changes may be made without departing from the scope of the disclosure.

Before the structures, systems, methods, and compositions for improving gastrointestinal function and reducing gas bubbles during a colonoscopy are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element, step, or ingredient not specified in the claim.

As used herein, the phrase "consisting essentially of" and grammatical equivalents thereof limit the scope of a claim to the specified ingredients, materials or steps and those that do not materially affect the basic and novel characteristic or characteristics of the claimed disclosure.

As used herein, "effective amount" means an amount of an ingredient or a component of the product that is nontoxic, but sufficient to provide the desired effect and performance at a reasonable benefit/risk ratio attending any dietary supplement or product. For example, an effective amount of a vitamin or mineral is an amount sufficient to prevent a deficiency thereof and to reduce the incidence of some adverse effects.

Unless defined otherwise, all technical and scientific terms used herein have the same meanings as commonly understood by one of ordinary skill in the art to which this disclosure pertains and belongs.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to particular embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Referring now to the figures, FIG. 1 illustrates the chemical formula of 6-gingerol, which is a form of gingerol. Gingerols are chemical compounds found in ginger root extract. Gingerols exhibit antioxidant, anti-tumor, and anti-inflammatory properties. Ginger root ex extract is shown to be effective at reducing or eliminating the presence of gas bubbles in the gastrointestinal tract.

Gingerols exhibit powerful medicinal properties. Specifically, gingerols reduce symptoms of nausea, including nausea associated with pregnancy or sea sickness. Gingerols may relieve nausea or vomiting induced by drugs such as general anesthesia or chemotherapy. Gingerols are effective against exercise-induced muscle pain and soreness and may reduce the time to recover from exercise-induced pain or injury. Additionally, gingerols exhibit anti-inflammatory effects and can reduce bone degeneration associated with osteoarthritis. Gingerols are associated with lower blood sugars and improving heart disease risk factors. Further, gingerols and other components of ginger root extract are shown to relieve symptoms of chronic indigestion and other ailments associated with the digestive system.

In an embodiment, a composition includes ginger root extract. The ginger root extract may include, for example, 6-gingerol and 6-shogaol. In an embodiment, the ginger root extract is dried ginger root 1:4 extract in 70% organic cane alcohol. In an embodiment, the ginger root extract is dried ginger root 1:4 extract in 60% organic cane alcohol. In an embodiment, the ginger root extract is dried ginger root 1:4 extract in 80% organic cane alcohol.

Figure 2:
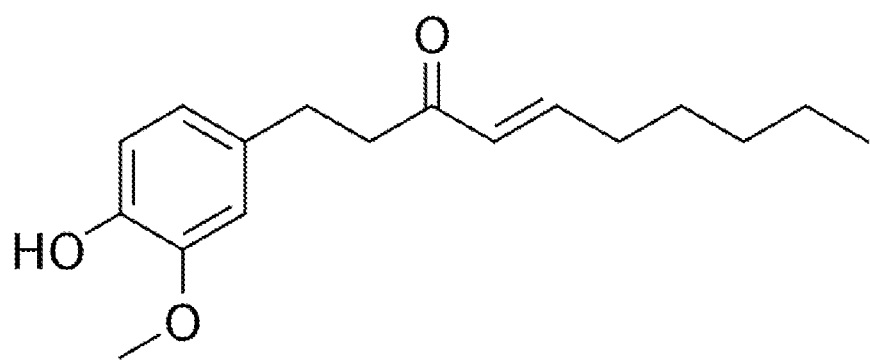
FIG. 2 illustrates the chemical formula of 6-shogael.

FIG. 2 illustrates the chemical formula of 6-shogaol, which is a form of shogaol. Shogaols are pungent constituents of ginger root extract similar in chemical structure to gingerols as shown in FIG. 1. Shogaols as a group include 4-shogaol, 6-shogaol, 10-shogaol, and 12-shogaol, which are all found in ginger. Shogaols are artifacts formed during storage or through excess heat and may be created by a dehydration reaction of gingerols.

Figure 3:
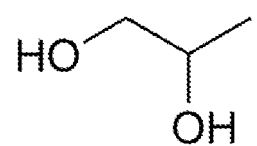
FIG. 3 illustrates the chemical formula of propylene glycol.

FIG. 3 illustrates the chemical formula of propylene glycol. The International Union of Pure and Applied Chemistry (IUPAC) name for propylene glycol is propane-1,2-diol. Propylene glycol is an organic compound with the chemical formula $CH_3CH(OH)CH_2OH$. Propylene glycol is a viscous, colorless liquid that includes two alcohol groups. Propylene glycol is miscible with a range of solvents, including water, acetone, and chloroform. In general, propylene glycol is non-irritation, has a low volatility, and a very low toxicity. Propylene glycol is chiral is sometimes referred to as α-propylene glycol to distinguish from the isomer propane-1,3-diol, known as β-propylene glycol.

The oral toxicity of propylene glycol is very low, and large quantities are required to cause perceptible health effects in humans. Propylene glycol is metabolized in the human body into pyruvic acid as a normal part of the glucose-metabolism process, acetic acid, lactic acid, and propionaldehyde. The potential for long-term oral toxicity of propylene glycol is low and the substance is therefore recognized as safe. Propylene glycol is essentially non-irritating to human skin and other human tissues.

Propylene glycol absorbs water and can be used a solvent. Because propylene glycol is water soluble, propylene glycol can be used in conjunction with ginger root extract and other components to reduce gas bubbles during a colonoscopy without negatively impacting the ability to clean and disinfect the colonoscope. In an embodiment, a composition comprising propylene glycol and ginger root extract is pushed through a colonoscope or another device to flush the colon during a colonoscopy. The composition is effective for reducing or eliminating gas bubbles that are naturally present in the gastrointestinal tract, and therefore, the composition is effective for improving visibility during a colonoscopy. The composition can easily be washed off the surfaces of the colonoscope after a procedure such that the colonoscope can be properly cleaned and disinfected. This is a significant improvement over the traditional use of simethicone, as discussed above.

Figure 4:
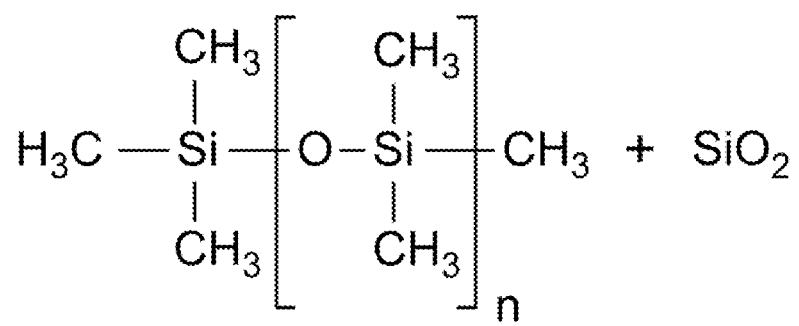
FIG. 4 illustrates the chemical formula of simethicone.

FIG. 4 illustrates the chemical formula of simethicone. Simethicone is traditionally used in preparation for and/or during colonoscopy procedures to reduce or eliminate the presence of gas bubbles in the gastrointestinal tract. Simethicone is shown to be effective for reducing or eliminating gas bubbles during a colonoscopy to improve visibility of the colon. However, simethicone is not water soluble and negatively impacts the effectiveness of cleaning and disinfecting a colonoscope after use. For this reason, simethicone can be the root cause of the transmission of disease during a colonoscopy and is therefore not safe for use with colonoscopes.

As discussed above, some gastrointestinal endoscopy practices use simethicone in an effort to improve visualizing during endoscopy. In this case, simethicone is typically diluted in a water container and injected into the patient via the endoscope's water channel or auxiliary water channel, or injected directly through the endoscope's instrument port with a syringe. Simethicone is difficult to remove from endoscopy equipment. Failure to remove simethicone during manual cleaning reduces the efficacy of the cleaning and disinfecting procedures. Simethicone is a form of silicone and is insoluble in both water and alcohol. In addition, solutions containing simethicone typically include sugars, thickeners, and binding agents. These ingredients can potentially support microbial and biofilm growth and are difficult to remove during cleaning and disinfecting procedures. For these reasons, endoscope manufacturers expressly discourage the use of simethicone in connection with endoscopes or colonoscopes.

Because simethicone is insoluble in both alcohol and water and is therefore difficult to remove from the surfaces of endoscopes and colonoscopes, there is a need for water soluble compositions that can effectively reduce or eliminate gas bubbles present in the gastrointestinal tract. Disclosed herein are compositions and methods for reducing or eliminating gas bubbles in the gastrointestinal tract without negatively impacting the ability to clean and disinfect endoscopy tools. The compositions disclosed herein may be ingested prior to a colonoscopy to prepare the gastrointestinal tract for the procedure. Additionally, the compositions disclosed herein may be injected into the patient during the colonoscopy procedure. The compositions may be injected directly via the colonoscope's water channel or auxiliary water channel, or directly through the endoscope's instrument port with a syringe. The compositions disclosed herein are water soluble and are therefore more easily absorbed by the body and cleaned off endoscopy instruments.

FIG. 5 is a schematic diagram of a method 500 for reducing the presence of gas bubbles in a gastrointestinal tract of a user during an endoscopy procedure. In an embodiment, the method 500 is performed by a medical practitioner or computer program during a colonoscopy procedure.

The method 500 begins and a medical practitioner or computer program administers at 502 a composition to a user during an endoscopy procedure, wherein the composition is effective for reducing the presence of gas bubbles in a gastrointestinal tract of the user. The method 500 is such that the composition includes an effective amount of ginger root extract for reducing the presence of the gas bubbles in the gastrointestinal tract of the user (see 504). The method 500 is such that the composition includes propylene glycol (see 506).

In an embodiment, administering the composition at 502 includes injecting the composition into the patient. The composition may be injected through a colonoscope to eliminate bubbles and improve visualization of the gastrointestinal tract. Flushes of the composition may be injected into the patient during an endoscopy procedure such as a colonoscopy. In an embodiment, the composition is administered at 502 by manually injecting flushes of the composition into the gastrointestinal tract of the user during the endoscopy procedure. In an embodiment, the composition is administered at 502 by flushing the composition during the endoscopy procedure through the irrigation and/or water channel of an endoscope such as a colonoscope. In an embodiment, the composition is administered at 502 by flushing the composition during the endoscopy procedure through an auxiliary water channel.

FIG. 6 is a schematic diagram of a method 600 for reducing the presence of gas bubbles in a gastrointestinal tract of a user during an endoscopy procedure. In an embodiment, the method 600 is performed by a medical practitioner or computer program during a colonoscopy procedure.

The method 600 begins and a medical practitioner or computer program causes a composition to be administered to a user during a colonoscopy procedure at 602. The composition is effective for reducing the presence of gas bubbles in a gastrointestinal tract of the user. The method 600 is such that the composition includes an effective amount of ginger root extract for reducing the presence of the gas bubbles in the gastrointestinal tract of the user (see 604). The method 600 is such that the composition include propylene glycol (see 606). The method 600 continues and a medical practitioner or computer program visualizes an interior of the gastrointestinal tract of the user with a colonoscope at 608. The method 600 continues and a medical practitioner or computer program causes the colonoscope to be processed to remove traces of the composition at 610. In an embodiment, the composition is water soluble such that the colonoscope can be rinsed or flushed to remove traces of the composition.

FIG. 7 is a schematic diagram of a method 700 for reducing the presence of gas bubbles in a gastrointestinal tract of a user during an endoscopy procedure. In an embodiment, the method 700 is performed by a medical practitioner or computer program during a colonoscopy procedure.

The method 700 begins and a medical practitioner or computer program causes a composition to be administered to a user during a colonoscopy procedure at 702. The composition is effective for reducing the presence of gas bubbles in a gastrointestinal tract of the user. The method 700 is such that the composition includes an effective amount of ginger root extract for reducing the presence of the gas bubbles in the gastrointestinal tract of the user (see 704). The method 700 is such that the composition include propylene glycol and sodium chloride (see 706). The method 700 continues and a medical practitioner or computer program visualizes an interior of the gastrointestinal tract of the user with a colonoscope at 708. The method 700 continues and a medical practitioner or computer program causes the colonoscope to be processed to remove traces of the composition at 710. In an embodiment, the composition is water soluble such that the colonoscope can be rinsed or flushed to remove traces of the composition.

EXAMPLES

The following examples pertain to further embodiments.

Table 1 below shows an example embodiment of the composition.

TABLE 1

| Component | Weight Percent Total Composition |
| --- | --- |
| Water | 59.6 |
| Propylene glycol | 20.3 |
| Ginger root extract | 11.2 |
| Citric acid | 4.6 |
| Ascorbic acid | 3.0 |
| Sodium chloride | 1.2 |
| Potassium sorbate | 0.1 |

Table 2 below shows an example embodiment of the composition.

TABLE 2

| Component | Weight Percent Total Composition |
| --- | --- |
| Water | 65.2 |
| Propylene glycol | 16.8 |
| Ginger root extract | 8.4 |
| Citric acid | 4.2 |
| Ascorbic acid | 4.2 |
| Sodium chloride | 1.1 |
| Potassium sorbate | 0.1 |

Table 3 below shows an example embodiment of the composition.

TABLE 3

| Component | Weight Percent Total Composition |
| --- | --- |
| Water | 55.7 |
| Propylene glycol | 19.4 |
| Ginger root extract | 15.7 |
| Citric acid | 3.2 |
| Ascorbic acid | 4.1 |
| Sodium chloride | 1.5 |
| Potassium sorbate | 0.4 |

Table 4 below shows an example embodiment of the composition.

TABLE 4

| Component | Weight Percent Total Composition |
| --- | --- |
| Water | 47.6 |
| Propylene glycol | 23.4 |
| Ginger root extract | 10.9 |
| Citric acid | 7.1 |
| Ascorbic acid | 8.5 |
| Sodium chloride | 2.5 |

Table 5 below shows an example embodiment of the composition.

TABLE 5

| Component | Weight Percent Total Composition |
| --- | --- |
| Water | 30.4 |
| Propylene glycol | 33.0 |
| Ginger root extract | 25.0 |
| Citric acid | 5.2 |
| Ascorbic acid | 4.8 |
| Sodium chloride | 1.6 |

Table 6 below shows an example embodiment of the composition.

TABLE 6

| Component | Weight Percent Total Composition |
| --- | --- |
| Water | 22.9 |
| Propylene glycol | 32.5 |
| Ginger root extract | 10.4 |
| Citric acid | 10.5 |
| Ascorbic acid | 9.1 |
| Sodium chloride | 14.6 |

According to one or more embodiments of the disclosure, a composition may include a combination of all of the following ingredients, or some, but not all, of the following ingredients:

a) Propylene glycol;
b) Ginger root extract;
c) 6-gingerol;
d) 6-shogaol;
e) Peppermint extract;
f) Citric acid;
g) Ascorbic acid;
h) Sodium chloride;
i) Potassium sorbate; and/or
j) Water.

Embodiments of the composition may comprise, for example, concentrations of propylene glycol as follows:
a1) from about 10 wt % to about 35 wt % the total composition;
a2) from about 10 wt % to about 45 wt % the total composition;
a3) from about 10 wt % to about 30 wt % the total composition;
a4) from about 10 wt % to about 25 wt % the total composition;
a5) from about 10 wt % to about 20 wt % the total composition;
a6) from about 10 wt % to about 15 wt % the total composition;
a7) from about 15 wt % to about 45 wt % the total composition;
a8) from about 20 wt % to about 45 wt % the total composition;
a9) from about 25 wt % to about 45 wt % the total composition;
a10) from about 30 wt % to about 45 wt % the total composition;
a11) from about 35 wt % to about 45 wt % the total composition;
a12) from about 40 wt % to about 45 wt % the total composition;
a13) from about 40 wt % to about 80 wt % the total composition;
a14) from about 30 wt % to about 90 wt % the total composition;
a15) from about 20 wt % to about 90 wt % the total composition;
a16) from about 45 wt % to about 80 wt % the total composition;
a17) from about 50 wt % to about 80 wt % the total composition;
a18) from about 60 wt % to about 80 wt % the total composition;
a19) from about 60 wt % to about 75 wt % the total composition;
a20) from about 60 wt % to about 70 wt % the total composition;
a21) from about 60 wt % to about 65 wt % the total composition;
a22) from about 50 wt % to about 70 wt % the total composition;
a23) from about 52 wt % to about 70 wt % the total composition;
a24) from about 54 wt % to about 70 wt % the total composition;
a25) from about 56 wt % to about 70 wt % the total composition;
a26) from about 58 wt % to about 70 wt % the total composition;
a27) from about 60 wt % to about 70 wt % the total composition;
a28) from about 62 wt % to about 70 wt % the total composition;

a29) from about 64 wt % to about 70 wt % the total composition;
a30) from about 66 wt % to about 70 wt % the total composition;
a31) from about 62 wt % to about 67 wt % the total composition;
a32) from about 63 wt % to about 67 wt % the total composition;
a33) from about 64 wt % to about 67 wt % the total composition; or
a34) from about 64 wt % to about 66 wt % the total composition.

Embodiments of the composition may comprise, for example, concentrations of ginger root extract as follows:
b1) from about 3 wt % to about 15 wt % the total composition;
b2) from about 3 wt % to about 14 wt % the total composition;
b3) from about 3 wt % to about 13 wt % the total composition;
b4) from about 3 wt % to about 12 wt % the total composition;
b5) from about 3 wt % to about 11 wt % the total composition;
b6) from about 3 wt % to about 10 wt % the total composition;
b7) from about 3 wt % to about 9 wt % the total composition;
b8) from about 4 wt % to about 15 wt % the total composition;
b9) from about 5 wt % to about 15 wt % the total composition;
b10) from about 6 wt % to about 15 wt % the total composition;
b11) from about 7 wt % to about 15 wt % the total composition;
b12) from about 8 wt % to about 15 wt % the total composition;
b13) from about 7 wt % to about 9 wt % the total composition;
b14) from about 6 wt % to about 10 wt % the total composition;
b15) from about 6 wt % to about 9 wt % the total composition;
b16) from about 5 wt % to about 12 wt % the total composition;
b17) from about 5 wt % to about 10 wt % the total composition;
b18) from about 2 wt % to about 20 wt % the total composition;
b19) from about 2 wt % to about 25 wt % the total composition;
b20) from about 2 wt % to about 30 wt % the total composition;
b21) from about 2 wt % to about 35 wt % the total composition;
b22) from about 2 wt % to about 40 wt % the total composition;
b23) from about 5 wt % to about 40 wt % the total composition;
b24) from about 5 wt % to about 45 wt % the total composition; or
b25) from about 5 wt % to about 50 wt % the total composition.

Embodiments of the composition may comprise, for example, concentrations of peppermint extract as follows:
e1) from about 3 wt % to about 15 wt % the total composition;
e2) from about 3 wt % to about 14 wt % the total composition;
e3) from about 3 wt % to about 13 wt % the total composition;
e4) from about 3 wt % to about 12 wt % the total composition;
e5) from about 3 wt % to about 11 wt % the total composition;
e6) from about 3 wt % to about 10 wt % the total composition;
e7) from about 3 wt % to about 9 wt % the total composition;
e8) from about 4 wt % to about 15 wt % the total composition;
e9) from about 5 wt % to about 15 wt % the total composition;
e10) from about 6 wt % to about 15 wt % the total composition;
e11) from about 7 wt % to about 15 wt % the total composition;
e12) from about 8 wt % to about 15 wt % the total composition;
e13) from about 7 wt % to about 9 wt % the total composition;
e14) from about 6 wt % to about 10 wt % the total composition;
e15) from about 6 wt % to about 9 wt % the total composition;
e16) from about 5 wt % to about 12 wt % the total composition;
e17) from about 5 wt % to about 10 wt % the total composition;
e18) from about 2 wt % to about 20 wt % the total composition;
e19) from about 2 wt % to about 25 wt % the total composition;
e20) from about 2 wt % to about 30 wt % the total composition;
e21) from about 2 wt % to about 35 wt % the total composition;
e22) from about 2 wt % to about 40 wt % the total composition;
e23) from about 5 wt % to about 40 wt % the total composition;
e24) from about 5 wt % to about 45 wt % the total composition; or
e25) from about 5 wt % to about 50 wt % the total composition.

Embodiments of the composition may comprise, for example, concentrations of citric acid as follows:
e1) from about 2 wt % to about 20 wt % the total composition;
e2) from about 2 wt % to about 19 wt % the total composition;
e3) from about 2 wt % to about 18 wt % the total composition;
e4) from about 2 wt % to about 17 wt % the total composition;
e5) from about 2 wt % to about 16 wt % the total composition;
e6) from about 2 wt % to about 15 wt % the total composition;
e7) from about 1 wt % to about 10 wt % the total composition;

e8) from about 2 wt % to about 10 wt % the total composition;
e9) from about 3 wt % to about 10 wt % the total composition;
e10) from about 4 wt % to about 10 wt % the total composition;
e11) from about 5 wt % to about 10 wt % the total composition;
e12) from about 1 wt % to about 9 wt % the total composition;
e13) from about 1 wt % to about 8 wt % the total composition;
e14) from about 1 wt % to about 7 wt % the total composition;
e15) from about 1 wt % to about 6 wt % the total composition;
e16) from about 2 wt % to about 5 wt % the total composition;
e17) from about 3 wt % to about 5 wt % the total composition;
e18) from about 1 wt % to about 15 wt % the total composition;
e19) from about 1 wt % to about 20 wt % the total composition;
e20) from about 1 wt % to about 25 wt % the total composition;
e21) from about 1 wt % to about 30 wt % the total composition; or
e22) from about 1 wt % to about 35 wt % the total composition.

Embodiments of the composition may comprise, for example, concentrations of ascorbic acid as follows:
g1) from about 2 wt % to about 20 wt % the total composition;
g2) from about 2 wt % to about 19 wt % the total composition;
g3) from about 2 wt % to about 18 wt % the total composition;
g4) from about 2 wt % to about 17 wt % the total composition;
g5) from about 2 wt % to about 16 wt % the total composition;
g6) from about 2 wt % to about 15 wt % the total composition;
g7) from about 1 wt % to about 10 wt % the total composition;
g8) from about 2 wt % to about 10 wt % the total composition;
g9) from about 3 wt % to about 10 wt % the total composition;
g10) from about 4 wt % to about 10 wt % the total composition;
g11) from about 5 wt % to about 10 wt % the total composition;
g12) from about 1 wt % to about 9 wt % the total composition;
g13) from about 1 wt % to about 8 wt % the total composition;
g14) from about 1 wt % to about 7 wt % the total composition;
g15) from about 1 wt % to about 6 wt % the total composition;
g16) from about 2 wt % to about 5 wt % the total composition;
g17) from about 3 wt % to about 5 wt % the total composition;
g18) from about 1 wt % to about 15 wt % the total composition;
g19) from about 1 wt % to about 20 wt % the total composition;
g20) from about 1 wt % to about 25 wt % the total composition;
g21) from about 1 wt % to about 30 wt % the total composition; or
g22) from about 1 wt % to about 35 wt % the total composition.

Embodiments of the disclosure may comprise, for example, concentrations of sodium chloride as follows:
h1) from about 1 wt % to about 30 wt % the total composition;
h2) from about 1 wt % to about 40 wt % the total composition;
h3) from about 1 wt % to about 25 wt % the total composition;
h4) from about 1 wt % to about 23 wt % the total composition;
h5) from about 1 wt % to about 20 wt % the total composition;
h6) from about 1 wt % to about 18 wt % the total composition;
h7) from about 1 wt % to about 15 wt % the total composition;
h8) from about 1 wt % to about 13 wt % the total composition;
h9) from about 1 wt % to about 10 wt % the total composition;
h10) from about 1 wt % to about 8 wt % the total composition;
h11) from about 1 wt % to about 5 wt % the total composition;
h12) from about 1 wt % to about 3 wt % the total composition;
h13) from about 1 wt % to about 2 wt % the total composition;
h14) from about 3 wt % to about 30 wt % the total composition;
h15) from about 5 wt % to about 30 wt % the total composition;
h16) from about 8 wt % to about 30 wt % the total composition;
h17) from about 10 wt % to about 30 wt % the total composition;
h18) from about 13 wt % to about 30 wt % the total composition;
h19) from about 15 wt % to about 30 wt % the total composition;
h20) from about 18 wt % to about 30 wt % the total composition;
h21) from about 20 wt % to about 30 wt % the total composition;
h22) from about 25 wt % to about 30 wt % the total composition;

The foregoing percentages, concentrations, and ratios are presented by example only and are not intended to be exhaustive or to limit the disclosure to the precise percentages, concentrations, and ratios disclosed. It should be appreciated that each value that falls within a disclosed range is disclosed as if it were individually disclosed as set forth herein. For example, a range indicating a weight percent from about 8% to about 14% additionally includes ranges beginning or ending with all values within that range, including for example a range beginning at 8.1%, 8.2%, 8.3%, 9%, 10%, 11%, 12%, and so forth.

Also, according to one or more non-limiting embodiments of the disclosure, any of the concentrations for ingredients for a combination of the ingredients (a) thru (i), for example, as listed above, may indicate the concentration for other ingredients listed above.

Example 1 is a composition. The composition includes an effective amount of ginger root extract for reducing gas bubbles in a gastrointestinal tract. The composition includes propylene glycol.

Example 2 is a composition as in Example 1, further comprising one or more of citric acid or ascorbic acid.

Example 3 is a composition as in any of Examples 1-2, further comprising one or more of sodium chloride or potassium sorbate.

Example 4 is a composition as in any of Examples 1-3, wherein the effective amount of the ginger root extract comprises from about 4 wt % to about 25 wt % the composition.

Example 5 is a composition as in any of Examples 1-4, wherein the propylene glycol comprises from about 10 wt % to about 30 wt % the composition.

Example 6 is a composition as in any of Examples 1-5, further comprising water, wherein the water comprises from about 50 wt % to about 85 wt % the composition.

Example 7 is a composition as in any of Examples 1-6, wherein the composition is prepared for oral administration.

Example 8 is a composition as in any of Examples 1-7, wherein the composition is prepared for intravenous or intramuscular administration.

Example 9 is a composition as in any of Examples 1-8, wherein the effective amount of the ginger root extract comprises 6-gingerol and 6-shogaol.

Example 10 is a composition as in any of Examples 1-9, wherein the composition is water soluble.

Example 11 is a method. The method includes providing a composition to a user for reducing gas bubbles in a gastrointestinal tract of the user. The composition includes an effective amount of ginger root extract for reducing the gas bubbles in the gastrointestinal tract of the user. The composition includes propylene glycol.

Example 12 is a method as in Example 11, wherein the composition further comprises one or more of citric acid or ascorbic acid.

Example 13 is a method as in any of Examples 11-12, wherein the composition further comprises one or more of sodium chloride or potassium sorbate.

Example 14 is a method as in any of Examples 11-13, wherein the effective amount of the ginger root extract comprises from about 4 wt % to about 25 wt % the composition.

Example 15 is a method as in any of Examples 11-14, wherein the propylene glycol comprises from about 10 wt % to about 30 wt % the composition.

Example 16 is a method as in any of Examples 11-15, wherein the composition further comprises water, and wherein the water comprises from about 50 wt % to about 85 wt % the composition.

Example 17 is a method as in any of Examples 11-16, wherein the composition is prepared for oral administration.

Example 18 is a method as in any of Examples 11-17, wherein the composition is prepared for intravenous or intramuscular administration.

Example 19 is a method as in any of Examples 11-18, wherein the effective amount of the ginger root extract comprises 6-gingerol and 6-shogaol.

Example 20 is a method as in any of Examples 11-19, wherein the composition is water soluble.

Example 21 is a method. The method includes administering a composition to a user during an endoscopy procedure. The composition includes an effective amount of ginger root extract for reducing a presence of gas bubbles in the gastrointestinal tract of the user. The composition includes propylene glycol.

Example 22 is a method as in Example 21, wherein the composition further comprises one or more of citric acid or ascorbic acid.

Example 23 is a method as in any of Examples 21-22, wherein the composition further comprises one or more of sodium chloride or potassium sorbate.

Example 24 is a method as in any of Examples 21-23, wherein the effective amount of the ginger root extract comprises from about 4 wt % to about 25 wt % the composition.

Example 25 is a method as in any of Examples 21-24, wherein the propylene glycol comprises from about 10 wt % to about 30 wt % the composition.

Example 26 is a method as in any of Examples 21-25, wherein the composition further comprises water, and wherein the water comprises from about 50 wt % to about 85 wt % the composition.

Example 27 is a method as in any of Examples 21-26, wherein the composition is prepared for oral administration.

Example 28 is a method as in any of Examples 21-27, wherein the composition is prepared for intravenous or intramuscular administration.

Example 29 is a method as in any of Examples 21-28, wherein the effective amount of the ginger root extract comprises 6-gingerol and 6-shogaol.

Example 30 is a method as in any of Examples 21-29, wherein the composition is water soluble.

Example 31 is a method as in any of Examples 21-30, wherein administering the composition comprises providing the composition to the user for consumption prior to the endoscopy procedure.

Example 32 is a method as in any of Examples 21-31, wherein administering the composition comprises flushing a large intestine of the user with the composition during the endoscopy procedure.

Example 33 is a method as in any of Examples 21-32, wherein flushing the large intestine of the user comprises injecting the composition into the large intestine of the user via a water channel and/or auxiliary channel of an endoscopic instrument used for performing the endoscopy procedure.

Example 34 is a method as in any of Examples 21-33, wherein flushing the large intestine of the user comprises directly injecting the composition into the large intestine of the user with a syringe.

Example 35 is a method as in any of Examples 21-34, further comprising cleaning an endoscopic device used for performing the endoscopy procedure by washing the endoscopic device with water.

Example 36 is a method as in any of Examples 21-35, further comprising cleaning an endoscopic device used for performing the endoscopy procedure by washing the endoscopic device with alcohol.

Example 37 is a method as in any of Examples 21-36, further comprising disinfecting an endoscopic device used for performing the endoscopy procedure such that the endoscopic device can be repurposed.

The foregoing description has been presented for purposes of illustration. It is not exhaustive and does not limit the invention to the precise forms or embodiments disclosed. Modifications and adaptations will be apparent to those skilled in the art from consideration of the specification and practice of the disclosed embodiments. For example, components described herein may be removed and other components added without departing from the scope or spirit of the embodiments disclosed herein or the appended claims.

Other embodiments will be apparent to those skilled in the art from consideration of the specification and practice of the disclosure disclosed herein. It is intended that the specification and examples be considered as exemplary only, with a true scope and spirit of the invention being indicated by the following claims.

What is claimed is:

1. A method for improving visibility of a gastrointestinal tract during an endoscopy procedure, the method comprising:
   administering a composition to a user prior to or during the endoscopy procedure, wherein the composition comprises:
   an effective amount of ginger root extract for reducing a presence of gas bubbles in the gastrointestinal tract of the user;
   propylene glycol; and
   sodium chloride.

2. The method of claim 1, wherein the composition further comprises one or more of citric acid or ascorbic acid.

3. The method of claim 1, wherein the composition does not comprise simethicone.

4. The method of claim 1, wherein the effective amount of the ginger root extract comprises from about 3 wt % to about 25 wt % the composition.

5. The method of claim 1, wherein the propylene glycol comprises from about 10 wt % to about 40 wt % the composition.

6. The method of claim 1, wherein the composition further comprises water, and wherein the water comprises from about 20 wt % to about 85 wt % the composition.

7. The method of claim 1, wherein the composition is administered to the user prior to the endoscopy procedure.

8. The method of claim 1, wherein the endoscopy procedure is a colonoscopy, and wherein administering the composition comprises flushing a large intestine of the user with the composition during the endoscopy procedure.

9. The method of claim 8, wherein flushing the large intestine of the user comprises injecting the composition into the large intestine of the user via a water channel and/or auxiliary channel of an endoscopic instrument used for performing the endoscopy procedure.

10. The method of claim 8, wherein flushing the large intestine of the user comprises directly injecting the composition into the large intestine of the user with a syringe.

11. The method of claim 1, wherein the effective amount of the ginger root extract comprises 6-gingerol and 6-shogaol.

12. The method of claim 1, wherein the composition is water soluble.

13. The method of claim 1, further comprising cleaning an endoscopic device used for performing the endoscopy procedure by washing the endoscopic device with water.

14. The method of claim 1, further comprising cleaning an endoscopic device used for performing the endoscopy procedure by washing the endoscopic device with alcohol.

15. The method of claim 1, further comprising disinfecting an endoscopic device used for performing the endoscopy procedure such that the endoscopic device can be repurposed.

* * * * *